United States Patent
Friedman

(10) Patent No.: US 6,320,162 B1
(45) Date of Patent: Nov. 20, 2001

(54) METHOD FOR PREHEATING DENTAL MATERIALS

(76) Inventor: Joshua Friedman, P.O. Box 2867, Danbury, CT (US) 06813

( * ) Notice: Subject to any disclaimer, the term of this patent is extended or adjusted under 35 U.S.C. 154(b) by 0 days.

(21) Appl. No.: 09/648,868

(22) Filed: Aug. 25, 2000

Related U.S. Application Data

(60) Continuation of application No. 09/452,502, filed on Dec. 1, 1999, now Pat. No. 6,236,020, which is a division of application No. 09/020,107, filed on Feb. 6, 1998, now abandoned.

(51) Int. Cl.$^7$ .............................. A61C 19/00; A61C 5/04; A61K 6/02; B29C 35/02
(52) U.S. Cl. .......................... 219/385; 219/386; 433/32; 433/226; 433/228.1
(58) Field of Search .................................... 219/385, 386; 433/32, 226, 228.1; 523/116

(56) References Cited

U.S. PATENT DOCUMENTS

| | | | |
|---|---|---|---|
| 2,269,874 | 1/1942 | Henschel | 126/261 |
| 3,902,043 | 8/1975 | Rogan | 219/242 |
| 4,092,138 | 5/1978 | Beitner | 62/3 |
| 4,287,408 | 9/1981 | Wilson | 219/475 |
| 4,361,528 | * 11/1982 | Ginsburg et al. | 264/28 |
| 4,924,070 | * 5/1990 | Friedman | 392/408 |
| 5,718,586 | * 2/1998 | Sharp et al. | 433/214 |
| 5,814,682 | 9/1998 | Rusin | 523/116 |
| 5,856,373 | 1/1999 | Kaisaki | 522/25 |
| 5,925,715 | 7/1999 | Mitra | 525/293 |
| 6,127,451 | * 10/2000 | Qian | 523/116 |

* cited by examiner

*Primary Examiner*—Joseph Pelham

(57) ABSTRACT

The present invention is a method for enhancing the cure of photocurable dental restorative composite(s) containing unreactive monomer(s) and filler upon exposure to light radiation comprising the steps of preheating the photocurable dental restorative composite(s) to an elevated temperature above ambient prior to said exposure to light radiation during clinical usage. The heating assembly of the present invention may be used to preheat any dental material(s) stored in one or more compules to an elevated temperature above ambient prior to clinical usage.

5 Claims, 8 Drawing Sheets

RELATIONSHIP BETWEEN PRE-CURE TEMPERATURE AND CONVERSION OF PHOTO-ACTIVATED RESIN COMPOSITE

RELATIONSHIP BETWEEN PRE-CURE TEMPERATURE AND CONVERSION OF PHOTO-ACTIVATED RESIN COMPOSITE

EFFECT OF COMPOSITE TEMPERATURE ON RESIN THICKNESS

EFFECT OF COMPOSITE TEMPERATURE ON THICKNESS

METHOD FOR PREHEATING DENTAL MATERIALS

This is a continuation application of U.S. patent application Ser. No. 09/452,502 filed Dec. 1, 1999, now U.S. Pat. No. , 6,236,020, which is a division application of U.S. patent application Ser. No. 09/020,107 filed Feb. 6, 1998, now abandoned.

FIELD OF THE INVENTION

This invention relates to a method and heating assembly for pre-heating dental material(s) prior to clinical usage and more particularly to a method and device for pre-heating compule(s) of dental material to an elevated temperature, above ambient, prior to clinical usage.

BACKGROUND OF INVENTION

In accordance with the present invention it has been discovered that many dental materials have properties which can be enhanced by being preheated just prior to clinical usage. Examples of such dental materials include etching agents, bleaching compositions, dental cements, impression materials and more particularly photocurable dental restorative materials. All such dental materials can be dispensed through a dispensing device such as a syringe. Presently, it has become conventional to package dental material(s) particularly dental restorative materials in unit dosage within a removable section hereafter called a "compule" of the dispensing device. The use of a dispenser facilitates the handling and discharge of the dental material(s) from the compule directly into the patient's mouth.

Photocurable dental restorative materials have become popular as a replacement for silver amalgams and have the advantage of matching the tooth color and being adjustable in the dental cavity for contour as well as shape before curing. Photocurable dental materials are composite compositions of unreactive monomer(s) and filler formulated to be polymerized by photochemical action upon exposure to light. In general photocurable restorative materials are typically formulated for dental usage as a paste and will polymerize upon the application of light in the 300–500 nanometer range. The concentration of filler in the composite is adjusted as high as possible to maximize strength, typically between 75–90% of the composition. The higher the filler concentration the more viscous and the more difficult the material is to dispense, handle and polymerize. Moreover, it is conventional for many dentists to refrigerate compules containing the photocurable dental restorative material prior to clinical use. The purpose of cold storage is to slow down the natural generation of free radicals within the material and thereby extend the useful life of the material. However, the viscosity of the composite is also subject to temperature and the colder the temperature the more viscous the material becomes. The ability of the photocurable material to flow and adapt to the intricacies of a dental cavity preparation will be compromised if sufficient time is not given to restore the temperature of the refrigerated composite back to room temperature.

SUMMARY OF THE INVENTION

It has been discovered in accordance with the present invention that when compules of photocurable composite materials are pre-heated to an elevated temperature above ambient immediately prior to clinical usage the degree of conversion i.e., the percentage of unreacted monomer converted to polymer within the cavity preparation is substantially increased. In addition, by pre-heating the compules of photocurable composite materials its viscosity is substantially reduced permitting yet higher filler loading(s) in the composite material and enabling the restorative material expressed from the compule to adapt better to the walls of the cavity preparation and to the intricacies of the cavity preparation.

The principle advantages of preheating compules of photocurable material(s) prior to clinical usage are as follows:

(1) Improved monomer conversion,
(2) Improved material hardness,
(3) Improved wear resistance,
(4) Improved color stability, and
(5) Improved strength.

Some or all of the same advantages apply when preheating dental material other than photocurable restorative material(s) prior to clinical usage. For example heating a bleaching composition containing a peroxide bleaching agent will be more active at higher temperatures. Thus the performance of many dental material(s) heated prior to clinical usage will be improved and their application time decreased in accordance with the present invention.

The method of the present invention for enhancing the cure of photocurable dental restorative composite materials containing unreactive monomer(s) and filler upon exposure to light radiation broadly comprises the step of preheating the photocurable dental restorative composite(s) to an elevated temperature above ambient prior to said exposure to light radiation during clinical usage.

The heating assembly of the present invention for heating dental materials prior to clinical usage comprises a base, an upper section removably mounted on the base for supporting one or more compules containing photocurable dental restorative composite material(s), with the upper section being composed of a conductive material and with the base forming a housing for a thermostat, a power connection for electrically connecting the thermostat to a source of power and a heating element for uniformity heating said upper section to an elevated temperature preset by said thermostat for preheating said compules to said elevated temperature.

BRIEF DESCRIPTION OF THE DRAWINGS

Other features and advantages of the present invention will become apparent from the following detailed description of the invention when read in conjunction with the accompanying drawings of which.

DETAILED DESCRIPTION OF THE PREFERRED EMBODIMENT

Figure 1:
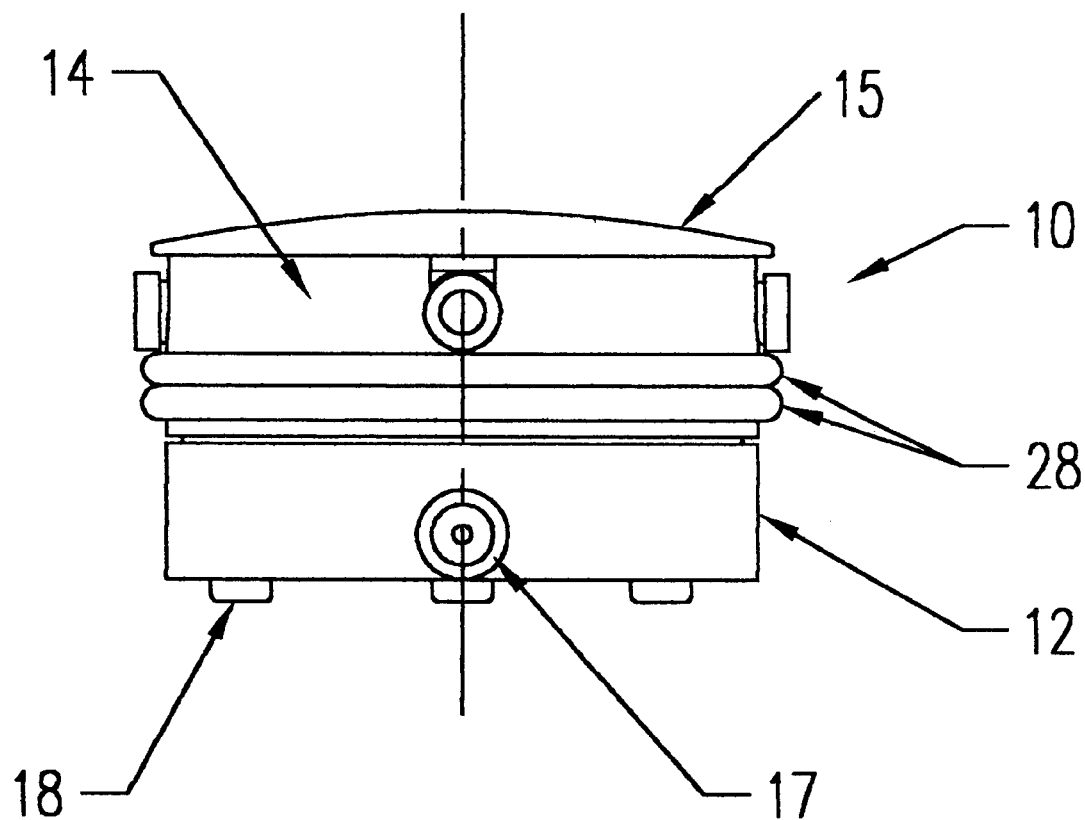
FIG. 1 is a perspective view of the heater assembly of the present invention.
Figure 2:
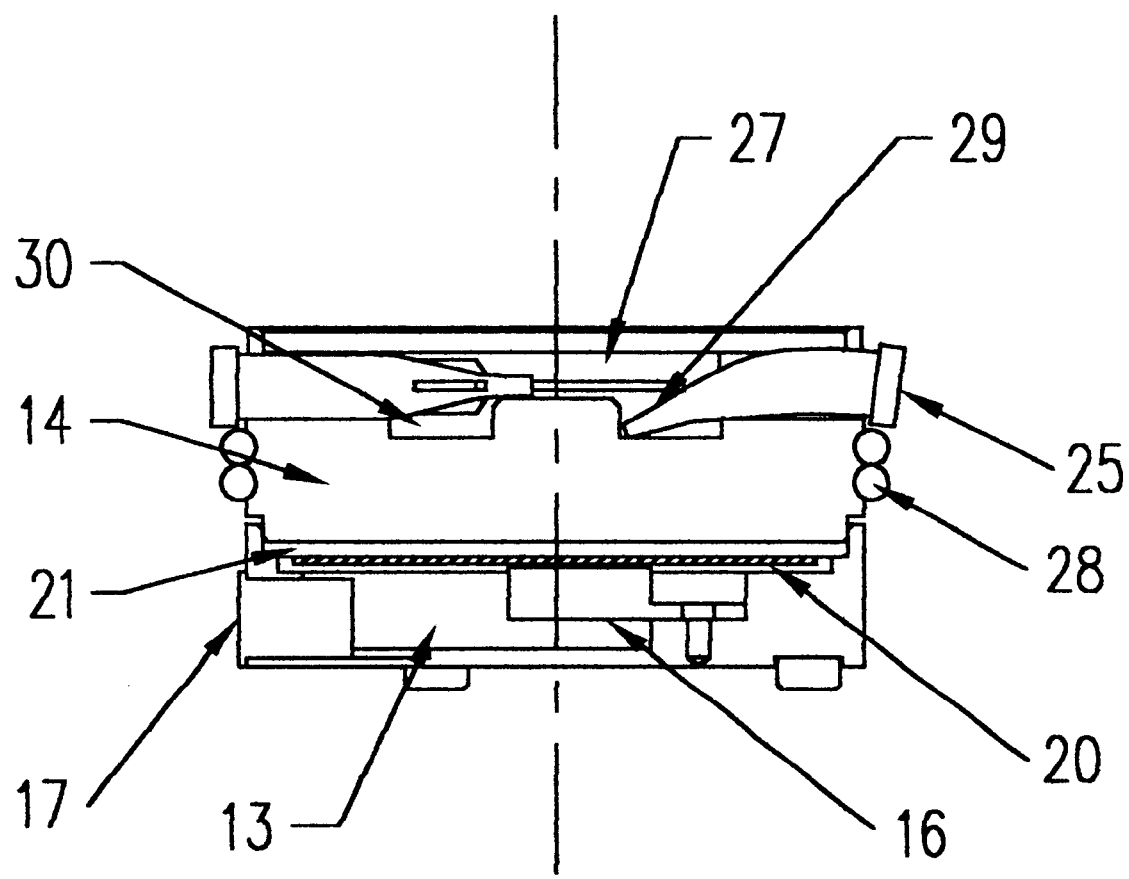
FIG. 2 is a cross sectional view of the heater assembly of FIG. 1.

The preferred heater assembly 10 of the present invention is shown in FIGS. 1,2,3,7 and 8 and comprises a base 12 having a removable upper section 14 mounted on the base 12 and a removable cover 15. The heater assembly 10 may be of any suitable geometry and size. In the embodiment of FIG. 1 the base 12 is cylindrical. The base 12 has a cavity 13 in which a thermostat 16 and a power connection 17 is mounted. The base 12 supports the removable upper section 14. The base 12 may be composed from any suitable material such as plastic or metal. The power connection 17 extends from the cavity 13 in the base 12 to the periphery 18 of the base 12 for electrically connecting the thermostat 16 to a suitable external source of electrical power (not shown). Although not shown the heater assembly 10 may also be operated from a rechargeable battery. The thermostat 16 may also be connected in circuit with a suitable visible light source (not shown) to provide a visual indication that the thermostat is operational and the unit has reached operating temperature.

The thermostat 16 is electrically connected to a heating element 20 to form an electrical resistive heater for heating the upper section 14 to a controlled temperature. The heating element 20 is a conductive material in the form of a filamentary wire or flat conductor of graphite, tungsten, copper or other suitable conductive material in a serpentine or other geometrical arrangement to form a series electrical path with the thermostat 16. The heating element 20 is embedded in a plastic, ceramic or rubber compound so as to form a flat surface which is connected to a conductive flat plate 21 upon which the upper section 14 rests. The flat plate 21 is removably affixed to the base 12 and provides a planar surface for uniformity heating the upper section 14 of the heating assembly 10. The thermostat 16 and heating element 20 are commercially available as a single unit. The thermostat 16 controls the temperature of the heating element 20. Any conventional type of thermostat may be used for this purpose and is preferably preadjusted to bring the temperature of the heating element 20 to a suitable elevated temperature above ambient room temperature but preferably between 100° F. and 140° F. The optimum temperature setting of the heating element 20 is about 130° F. for photocurable dental materials. It could be higher for bleaching or other dental materials applied to the enamel. Too high a temperature would cause dental pulp damage.

The removable upper section 14 of the heating assembly 10 is of a conductive material such as aluminum, copper, brass or stainless steel and rests upon the flat plate 21 which may be fabricated from a similar conductive material. One or more slots 22 is provided in the upper section 14 of the heater assembly 10 to support a corresponding number of compules 25 of photocurable restorative material. Once the upper section 14 is heated it serves as a heat sink upon its removal from the base 12 to maintain the compules at a relatively uniform temperature over an extended time period. In the embodiment of FIG. 1 four compules 25 are shown symmetrically arranged in slots 22 positioned 90° apart from one another. The cover 15 is seated over the heater assembly 10 to substantially enclose the compules 25 within an enclosed space 27 to facilitate the heating of the compules 25. An insulating member 28, preferably rubber or plastic O-ring(s), surrounds the upper section 14 to enable the upper section 14 to be removed from the base 12 to a dental tray adjacent the patient at the elevated temperature to which the compules 25 have been raised.

Figure 3:
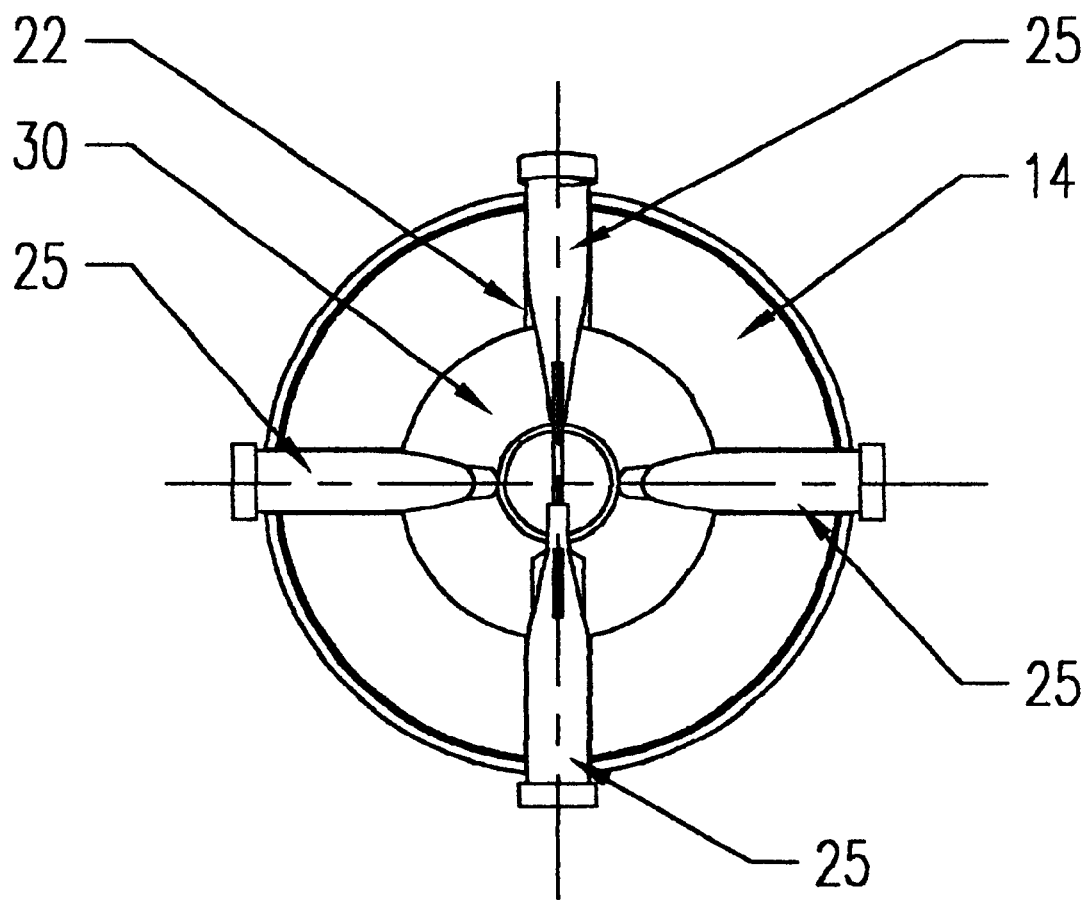
FIG. 3 is a top view of the heater assembly of FIG. 1 with the cover removed.
Figure 7:
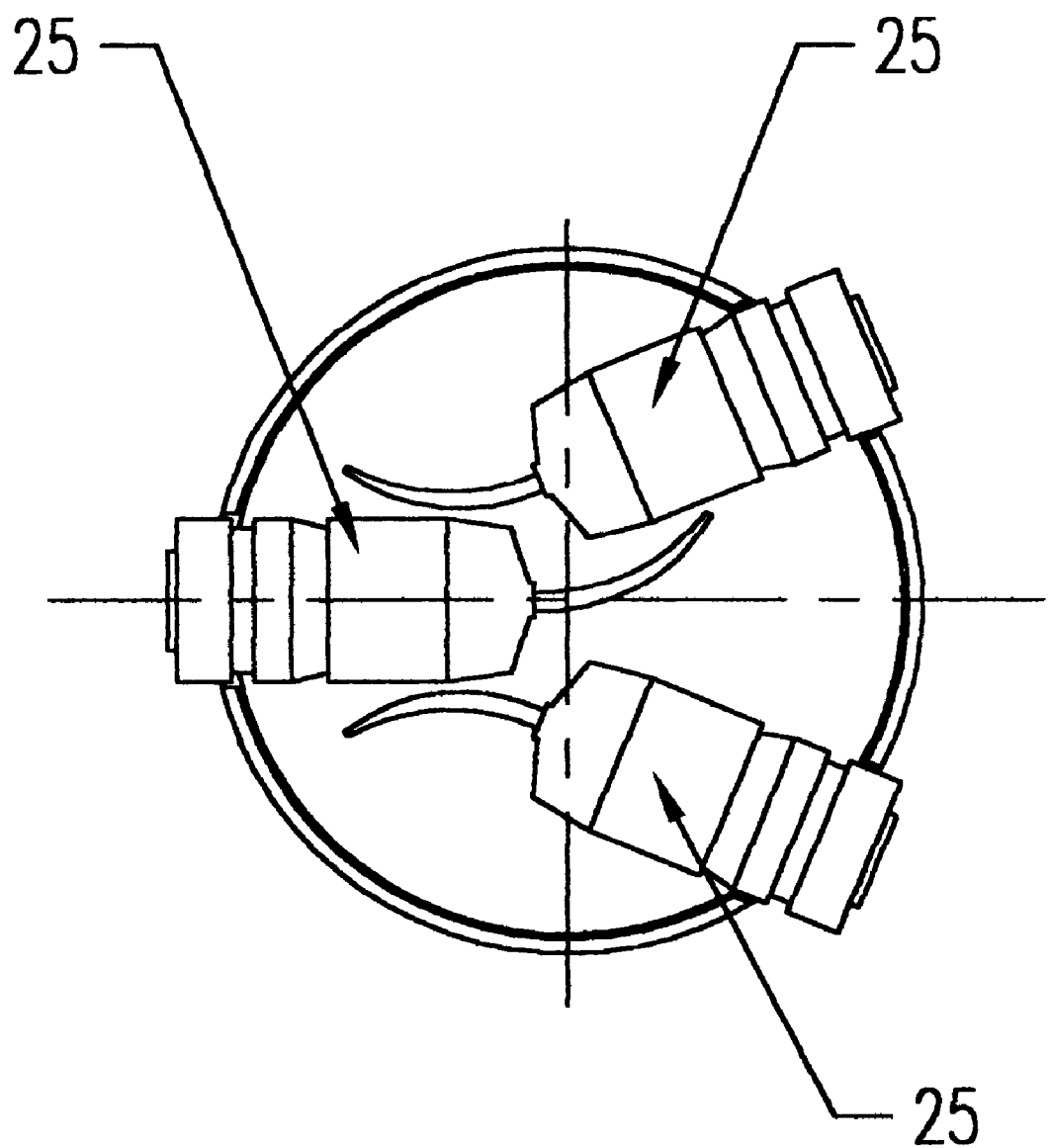
FIG. 7 shows an alternative compule arrangement for the heater assembly of FIG. 1.
Figure 8:
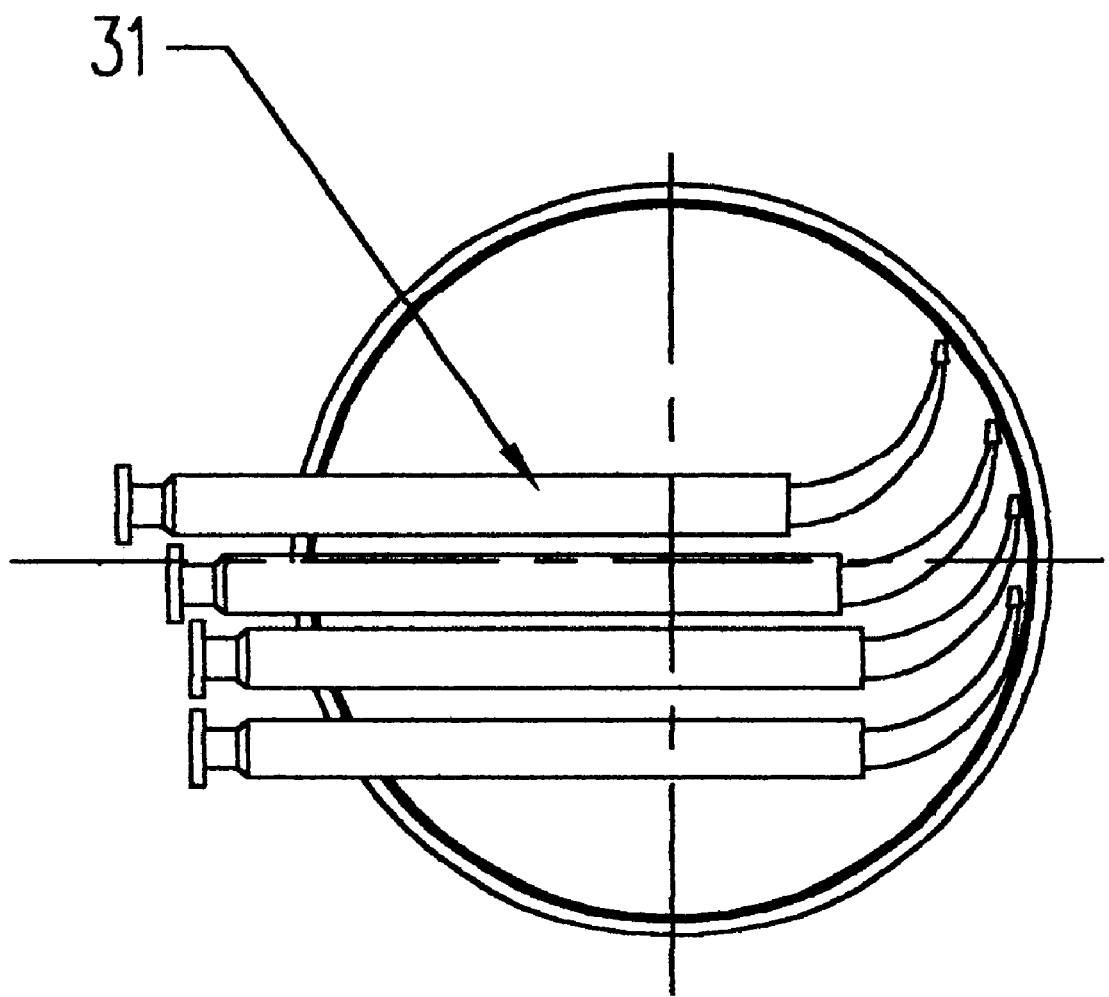
FIG. 8 shows yet another alternative compule arrangement using small syringe compules with the heater assembly of the present invention.

The design of the individual compules 25 does not form a part of the present invention. Different compule designs are available commercially for conventional use with different dispensers. The compules 25 are generally affixed to the end of the dispenser and have a contoured shape with an open ended tip 29 at the distal end thereof which lies at an appropriate angle from the central axis of the compule 25. Photocurable material is discharged into a dental cavity from the compules 25 as shown in FIG. 3 and FIG. 7 by attachment of each compule to a conventional dispensing syringe. Alternatively as shown in FIG. 8 the heating assembly may be used to heat a combination compule syringe dispenser 31. Such combination compule syringe dispenser (s) 31 are presently commercially available. The upper section 14 of the heating assembly contains an annular channel 30 for receiving the tips 29 of the compules 25. FIGS. 7 and 8 show alternate arrangements to accommodate different compule/syringe designs.

Figure 4:
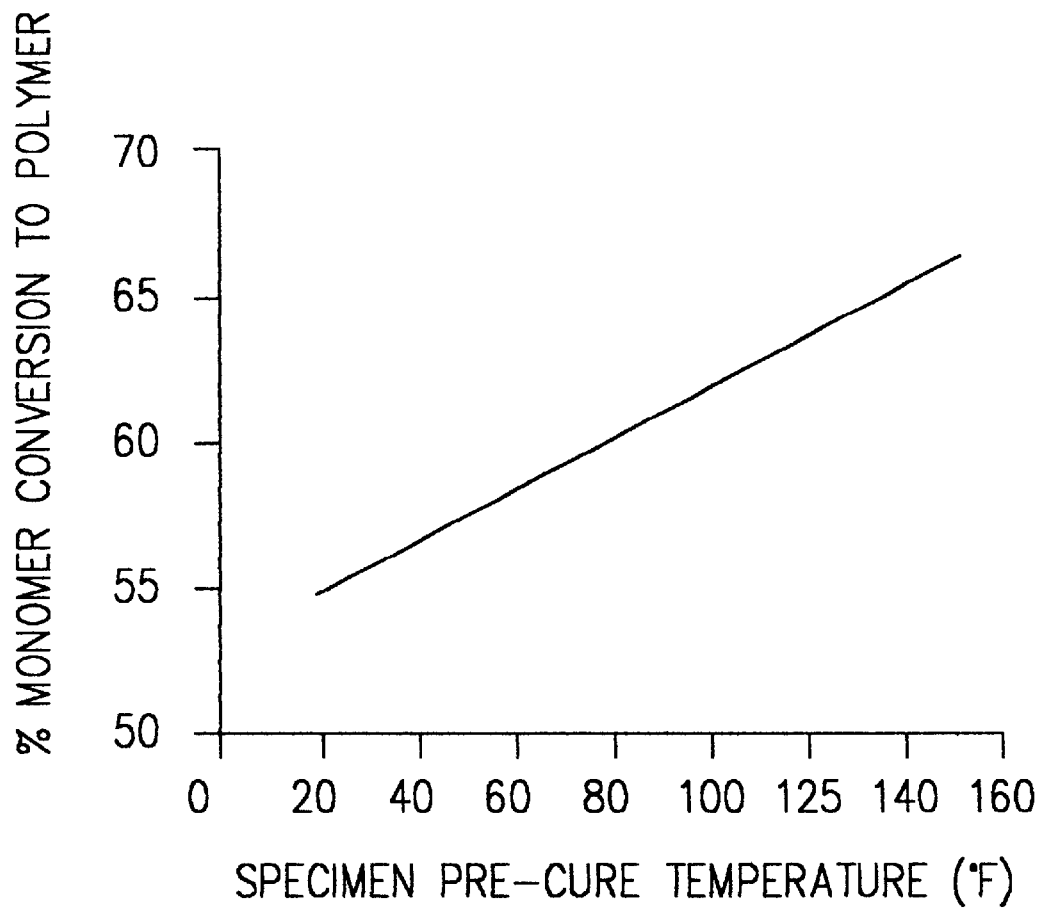
FIG. 4 is a graph showing the relationship between pre-cure temperature and percentage of monomer conversion into polymer.
Figure 5:
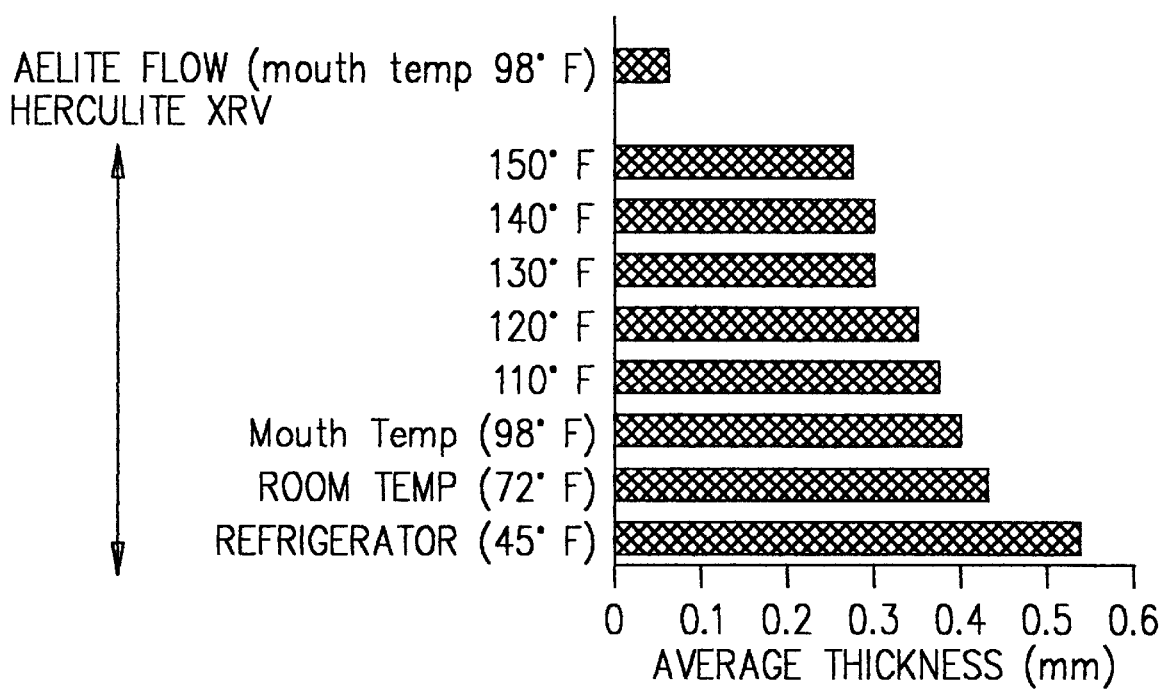
FIG. 5 is another graph showing the effect of different temperatures on the viscosity of a typical composite dental resin material before cure with viscosity differences shown by measuring the average thickness variation of the material at each temperature.
Figure 6:
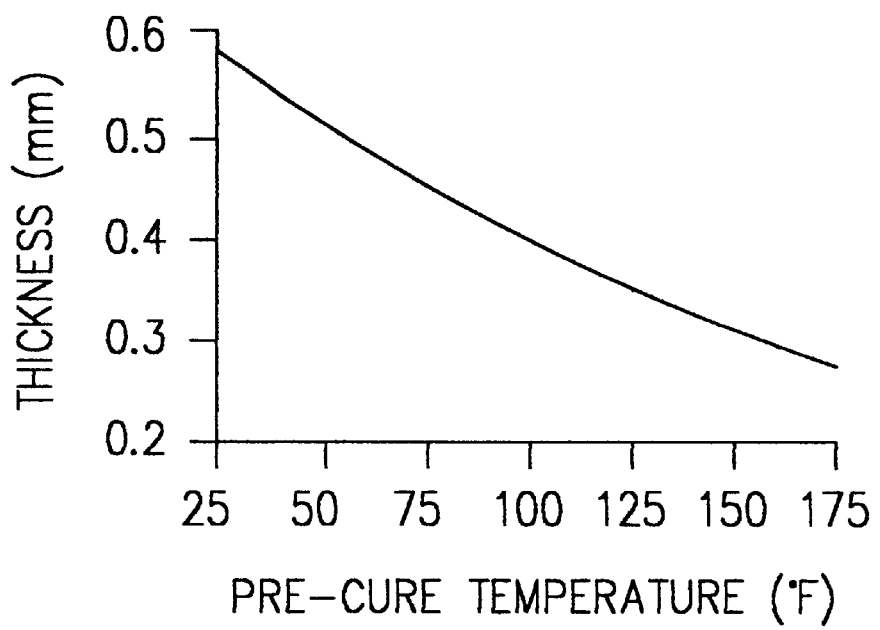
FIG. 6 is yet another graph similar to FIG. 5 which shows that the relationship of temperature and the viscosity (measured by thickness variation) of the pre-cured dental material is non-linear.

In accordance with the present invention it was discovered that the reactive monomer in the photocurable material converts to polymer in a substantially linear relationship over a temperature range extending from a refrigerated temperature of 20° F. to an elevated temperature of 150° F. This was substantiated by the graphically presented data in FIG. 4 using a commercially common photo-activated composite identified as Herculite XRV, shade A2, manufactured by Kerr/Sybron of Orange Calif. A small amount of material was expressed between two mylar strips and conditioned for a minimum of 30 minutes at selected pre-set temperature values. A conventional dental light curing unit was also placed in each temperature environment. While in this environment the test specimen was exposed to a controlled intensity (500 mW/cm$^2$) of curing light for 60 seconds. Following exposure the specimen was stored in the dark for 24 hours. The extent of monomer conversion was then determined by using an infrared spectrometer (FTIR) and standardized methods of statistical analysis. FIG. 4 shows the relationship of monomer conversion to pre-cure temperature. FIGS. 5 and 6 show the effect of temperature on viscosity with viscosity measured by the thickness variation of the material, i.e., a less viscous material will have less thickness. FIGS. 5 and 6 validate the concept of the present invention that an increase in the temperature of photocurable materials above ambient temperature and particularly above 100° F. and optimally at 130° F. prior to clinical usage unexpectedly enhances cure.

What is claimed is:

1. A method for enhancing the cure of photocurable dental restorative composite(s) containing unreactive monomer(s) and filler upon exposure to light radiation comprising the steps of preheating the photocurable dental restorative composite(s) to an elevated temperature above ambient prior to said exposure to light radiation during clinical usage.

2. A method as defined in claim 1 wherein said dental restorative composite(s) containing unreactive monomer(s) and filler are preheated to said elevated temperature in a compule to be dispensed through a syringe.

3. A method as defined in claim 2 wherein said compule is preheated to a preset temperature between about 100° F. to 140° F.

4. A method as defined in claim 3 wherein said compule is preheated to a preset temperature of about 130° F.

5. A method as defined in claim 3 wherein said dental restorative composite material is discharged from said compule using a dispensing syringe.

* * * * *